United States Patent
Ikeda et al.

(10) Patent No.: US 8,242,052 B2
(45) Date of Patent: Aug. 14, 2012

(54) METHOD FOR CONTROLLING NOXIOUS ORGANISMS

(75) Inventors: Hajime Ikeda, Kobe (JP); Atsushi Iwata, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 364 days.

(21) Appl. No.: 12/562,957

(22) Filed: Sep. 18, 2009

(65) Prior Publication Data

US 2010/0317523 A1 Dec. 16, 2010

(30) Foreign Application Priority Data

Jun. 12, 2009 (JP) ................................. 2009-140959
Jul. 15, 2009 (JP) ................................. 2009-166508

(51) Int. Cl.
*A01N 25/26* (2006.01)
(52) U.S. Cl. ...................................................... 504/100
(58) Field of Classification Search .................. None
See application file for complete search history.

(56) References Cited

FOREIGN PATENT DOCUMENTS

| WO | WO-00/27203 A1 | 5/2000 |
| WO | WO-03/096811 | * 11/2003 |
| WO | WO-03/096811 A1 | 11/2003 |
| WO | WO-2005/009128 A1 | 2/2005 |

* cited by examiner

*Primary Examiner* — Alton Pryor
(74) *Attorney, Agent, or Firm* — Birch, Stewart, Kolasch & Birch, LLP

(57) ABSTRACT

A method for controlling noxious organisms in a field of soybean or corn, comprising the steps of:
   treating soybean or corn seeds with at least one neonicotinoid compound selected from the group consisting of clothianidin, thiamethoxam, imidacloprid, dinotefuran, nitenpyram, acetamiprid, and thiacloprid, and
   treating the field with at least one PPO inhibitor compound selected from the group consisting of flumioxazin, sulfentrazone, saflufenacil, oxyfluorfen, and 3-(4-chloro-6-fluoro-2-trifluoromethylbenzimidazol-7-yl)-1-methyl-6-trifluoromethyl-2,4-(1H,3H)pyrimidinedione before or after the soybean or corn seeds treated with the neonicotinoid compound are sown in the field.

9 Claims, No Drawings

METHOD FOR CONTROLLING NOXIOUS ORGANISMS

BACKGROUND OF THE INVENTION

1. Field of the Invention

The present invention relates to a method for controlling noxious organisms, namely harmful arthropods and weeds.

2. Description of the Related Art

Neonicotinoid compounds are known as an active ingredients for insecticides. In addition, PPO inhibitor compounds are also known as an active ingredients for herbicides.

PRIOR ART DOCUMENT

Non-patent Document 1: Crop Protection Handbook, vol. 89 (2003)

SUMMARY OF THE INVENTION

The present invention provides a method which shows excellent controlling effects on noxious organisms in a field of soybean or corn by using a neonicotinoid compound and a PPO inhibitor compound.

The present invention comprises treating soybean or corn seeds with a neonicotinoid compound before or after the field where the seeds are to be sown is treated with a PPO inhibitor compound, so that excellent noxious organism control effects on harmful arthropods and weeds occurring in the field can be exhibited.

The present invention relates to the followings.

[1] A method for controlling noxious organisms in a field of soybean or corn, comprising the steps of:

treating soybean or corn seeds with at least one neonicotinoid compound selected from the group consisting of clothianidin, thiamethoxam, imidacloprid, dinotefuran, nitenpyram, acetamiprid, and thiacloprid, and treating the field with at least one PPO inhibitor compound selected from the group consisting of flumioxazin, sulfentrazone, saflufenacil, oxyfluorfen, and 3-(4-chloro-6-fluoro-2-trifluoromethylbenzimidazol-7-yl)-1-methyl-6-trifluoromethyl-2,4-(1H,3H)pyrimidinedione before or after the soybean or corn seeds treated with the neonicotinoid compound are sown in the field.

[2] The method for controlling noxious organisms according to item [1], comprising the steps of:

treating soybean or corn seeds with at least one neonicotinoid compound selected from the group consisting of clothianidin, thiamethoxam, imidacloprid, dinotefuran, nitenpyram, acetamiprid, and thiacloprid, and treating the field with at least one PPO inhibitor compound selected from the group consisting of flumioxazin, sulfentrazone, saflufenacil, oxyfluorfen, and 3-(4-chloro-6-fluoro-2-trifluoromethylbenzimidazol-7-yl)-1-methyl-6-trifluoromethyl-2,4-(1H,3H)pyrimidinedione before the soybean or corn seeds treated with the neonicotinoid compound are sown in the field.

[3] The method for controlling noxious organisms according to item [1], comprising the steps of:

treating soybean or corn seeds with at least one neonicotinoid compound selected from the group consisting of clothianidin, thiamethoxam, imidacloprid, dinotefuran, nitenpyram, acetamiprid, and thiacloprid, and treating the field with at least one PPO inhibitor compound selected from the group consisting of flumioxazin, sulfentrazone, saflufenacil, oxyfluorfen, and 3-(4-chloro-6-fluoro-2-trifluoromethylbenzimidazol-7-yl)-1-methyl-6-trifluoromethyl-2,4-(1H,3H)pyrimidinedione after the soybean or corn seeds treated with the neonicotinoid compound are sown in the field.

[4] A method for controlling noxious organisms in a field of soybean, comprising the steps of:

treating soybean seeds with at least one neonicotinoid compound selected from the group consisting of clothianidin, thiamethoxam, imidacloprid, dinotefuran, nitenpyram, acetamiprid, and thiacloprid, and treating the field with at least one PPO inhibitor compound selected from the group consisting of flumioxazin, sulfentrazone, saflufenacil, oxyfluorfen, and 3-(4-chloro-6-fluoro-2-trifluoromethylbenzimidazol-7-yl)-1-methyl-6-trifluoromethyl-2,4-(1H,3H)pyrimidinedione before or after the soybean seeds treated with the neonicotinoid compound are sown in the field.

[5] A method for controlling noxious organisms in a field of corn, comprising the steps of:

treating corn seeds with at least one neonicotinoid compound selected from the group consisting of clothianidin, thiamethoxam, imidacloprid, dinotefuran, nitenpyram, acetamiprid, and thiacloprid, and treating the field with at least one PPO inhibitor compound selected from the group consisting of flumioxazin, sulfentrazone, saflufenacil, oxyfluorfen, and 3-(4-chloro-6-fluoro-2-trifluoromethylbenzimidazol-7-yl)-1-methyl-6-trifluoromethyl-2,4-(1H,3H)pyrimidinedione before or after the corn seeds treated with the neonicotinoid compound are sown in the field.

[6] The method for controlling noxious organisms according to any one of items [1] to [5], wherein the noxious organisms are harmful arthropods.

[7] The method for controlling noxious organisms according to any one of items [1] to [5], wherein the noxious organisms are weeds.

[8] The method for controlling noxious organisms according to anyone of items [1] to [7], wherein the neonicotinoid compound is clothianidin or thiamethoxam.

[9] The method for controlling noxious organisms according to anyone of items [1] to [7], wherein the neonicotinoid compound is clothianidin.

[10] The method for controlling noxious organisms according to any one of items [1] to [9], wherein the PPO inhibitor compound is flumioxazin, sulfentrazone, or saflufenacil.

[11] The method for controlling noxious organisms according to any one of items [1] to [9], wherein the PPO inhibitor compound is flumioxazin.

Noxious organisms in a soybean field or a corn field can be controlled by the method for controlling noxious organisms according to the present invention.

DETAILED DESCRIPTION OF PREFERRED EMBODIMENTS

The method for controlling noxious organisms according to the present invention includes the steps of:

(1) treating soybean or corn seeds with at least one neonicotinoid compound selected from the group consisting of clothianidin, thiamethoxam, imidacloprid, dinotefuran, nitenpyram, acetamiprid, and thiacloprid, and (2) treating the field with at least one PPO inhibitor compound selected from the group consisting of flumioxazin, sulfentrazone, saflufenacil, oxyfluorfen, and 3-(4-chloro-6-fluoro-2-trifluoromethylbenzimidazol-7-yl)-1-methyl-6-trifluoromethyl-2,4-(1H,3H)pyrimidinedione before or after the soybean or corn seeds treated with the neonicotinoid compound are sown in the field.

(1) The step of treating soybean or corn seeds with at least one neonicotinoid compound selected from the group consisting of clothianidin, thiamethoxam, imidacloprid, dinotefuran, nitenpyram, acetamiprid, and thiacloprid In the present invention, the soybean seed and the corn seed are not particularly limited so long as they belong to cultivars which are generally cultivated as crop plants.

Examples of such plant cultivars include those to which resistance to herbicides has been imparted by a classical breeding method, a genetic engineering technique or the like, such herbicides being an inhibitor of 4-hydroxyphenylpyruvic acid dioxygenase (hereinafter referred to as HPPD) (e.g. isoxaflutole), an inhibitor of acetolactate synthase (hereinafter referred to as ALS)(e.g. imazethapyr, thifensulfuron-methyl), an inhibitor of 5-enolpyruvylshikimate-3-phosphate synthase (e.g. glyphosate), an inhibitor of glutamine synthase (e.g. glufosinate), an auxin type herbicide (e.g. 2,4-D, dicamba), or bromoxynil.

Examples of the crop plant to which resistance to a herbicide has been imparted by a classical breeding method include corn which is resistant to an imidazolinone type ALS inhibitor herbicide (e.g. imazethapyr) and which has already been commercially available under the trade name of Clearfield (registered trademark). Such a crop plant also includes STS soybean which is resistant to a sulfonylurea type ALS inhibitor herbicide such as thifensulfuron-methyl. Similarly, examples of the crop plant to which resistance to an acetyl CoA carboxylase inhibitor such as a trione oxime or aryloxyphenoxypropionic acid herbicide has been imparted by a classical breeding method include SR corn. Crop plants to which resistance to an acetyl CoA carboxylase inhibitor has been imparted are described in Proc. Natl. Acad. Sci. USA (1990), 87, 7175-7179.

Examples of the crop plant to which resistance to a herbicide has been imparted by a genetic engineering technique include corn cultivars and soybean cultivars, each having resistance to glyphosate, and such corn and soybean cultivars are already sold under the trade names of Roundup Ready (registered trademark), Agrisure GT, and the like. Similarly, such crop plants to which resistance to a herbicide has been imparted by a genetic engineering technique include corn cultivars and soybean cultivars, each having resistance to glufosinate, and they are already sold under the trade name of LibertyLink (registered trademark), and the like. There are corn cultivars and soybean cultivars which are resistant to both glyphosate and ALS inhibitors, and they are sold under the trade name of Optimum GAT (registered trademark).

Mutant acetyl CoA carboxylase which is resistant to an acetyl CoA carboxylase inhibitor has been reported in Weed Science (2005) vol. 53, pp. 728-746, and a crop plant having resistance to an acetyl CoA carboxylase inhibitor can be produced when a gene encoding the mutant acetyl CoA carboxylase is introduced into a crop plant by a genetic engineering technique or when a mutation related to impartation of resistance is introduced into a gene encoding acetyl CoA carboxylase of a crop plant. Further, nucleic acids for introduction of a base substitution mutation can be introduced into cells of a crop plant by chimeraplasty (Gura T. 1999, Repairing the Genome's Spelling Mistakes, Science 285: 316-318) to induce a site-directed amino acid substitution mutation in the gene of acetyl CoA carboxylase or the ALS gene of the crop plant, whereby a crop plant resistant to an acetyl CoA carboxylase inhibitor or an ALS inhibitor can be produced.

A soybean crop plant resistant to dicamba can be produced by introducing a gene of dicamba-degrading enzyme such as dicamba monooxygenase isolated from *Pseudomonas maltophilia* into the plant (Behrens et al. 2007 Dicamba Resistance: Enlarging and Preserving Biotechnology-Based Weed Management Strategies. Science 316: 1185-1188).

A crop plant resistant to both to a phenoxy acid herbicide (e.g. 2,4-D, MCPA, dichlorprop, or mecoprop) and an aryloxyphenoxypropionic acid herbicide (e.g. quizalofop, haloxyfop, fluazifop, dichlorfop, fenoxaprop, metamifop, cyhalofop, or clodinafop) can be produced by introducing a gene encoding an aryloxyalkanoate dioxygenase (WO 2005/107437, WO 2007/053482, WO 2008/141154).

A crop plant resistant to HPPD inhibitors can be produced by introducing a gene encoding HPPD which shows resistance to HPPD inhibitors (US2004/0058427).

Moreover, a crop plant resistant to herbicides can be produced by introducing genes described in WO98/20144, WO2002/46387, and US2005/0246800.

The above-described crop plants include those to which an ability to produce a selective toxin which is known to be produced by *Bacillus*, has been imparted by a genetic engineering technique. Examples of the toxin which is produced by such a genetically engineered crop plant include insecticidal proteins derived from *Bacillus cereus* and *Bacillus popilliae*; δ-endotoxins (e.g. Cry1Ab, Cry1Ac, Cry1F, Cry1Fa2, Cry2Ab, Cry3A, Cry3Bb1 and Cry9C) and insecticidal proteins (e.g. VIP 1, VIP 2, VIP 3 and VIP 3A), derived from *Bacillus thuringiensis*; insecticidal proteins derived from nematodes; toxins produced by animals, such as scorpion toxins, spider toxins, bee toxins and insect-specific nerve toxins; fungal toxins; plant lectin; agglutinin; protease inhibitors such as trypsin inhibitors, serine protease inhibitors, patatin, cystatin, and papain inhibitors; ribosome-inactivating proteins (RIP) such as ricin, corn-RIP, abrin, luffin, saporin, and briodin; steroid metabolizing enzymes such as 3-hydroxysteroid oxidase, ecdysteroid-UDP-glucosyltransferase, and cholesterol oxidase; ecdysone inhibitors; HMG-CoA reductase; ion channel inhibitors such as sodium channel inhibitors and calcium channel inhibitors; juvenile hormone esterase; diuretic hormone receptors; stilbene synthase; bibenzyl synthase; chitinase; and glucanase; and the like.

In addition, the insecticidal toxin which is expressed in such a genetically engineered crop plant also includes hybrid toxins of δ-endotoxin proteins such as Cry1Ab, Cry1Ac, Cry1F, Cry1Fa2, Cry2Ab, Cry3A, Cry3Bb1, Cry9C, Cry34Ab and Cry35Ab, and insecticidal proteins such as VIP 1, VIP 2, VIP 3 and VIP 3A, and toxins in which a part is deleted or modified. The hybrid toxin is made by newly combining different domains of the insecticidal proteins with use of a genetic engineering technique. Cry1Ab in which a part of an amino acid sequence is deleted is known as an example of such a toxin in which a part is deleted. An example of the toxin in which a part is modified is a toxin in which one or more of amino acids of a naturally occurring toxin are substituted. The insecticidal toxin and the genetically engineered crop plant having an ability to synthesize the insecticidal toxin are described in EP-A-0374753, WO 93/07278, WO 95/34656, EP-A-0427529, EP-A-451878, WO03/052073, and the like. Such a toxin contained in these genetically engineered crop plants imparts to a plant resistance particularly to a coleopteran pest, a dipteran pest or a lepidopteran pest.

Moreover, genetically engineered crop plants which have one or more pest-resistant genes and thereby express one or more insecticidal toxins are also known, and some of them are commercially available. Examples of such genetically engineered crop plants include YieldGard (registered trademark) (a corn cultivar expressing Cry1Ab toxin), YieldGard Rootworm (registered trademark) (a corn cultivar expressing Cry3Bb1 toxin), YieldGard Plus (registered trademark) (a corn cultivar expressing Cry1Ab and Cry3Bb1 toxins), Herculex I (registered trademark) (a corn cultivar expressing Cry1Fa2 toxin and phosphinothricin N-acetyltransferase (PAT) for imparting resistance to gluphosinate), NatureGard (registered trademark) Agrisure (registered trademark) GT Advantage (a GA21 glyphosate resistant character), Agrisure (registered trademark) CB Advantage (a Bt11 corn borer (CB) character), Protecta (registered trademark), and the like.

Examples of the plant used in the present invention include a plant such as soybean having aphid resistance which is imparted by introducing, for example, the Rag 1 (Resistance Aphid Gene 1) gene.

The above-described crop plants also include those to which an ability to produce an anti-pathogen substance having a selective action has been imparted by a genetic engineering technique. The known examples of such an anti-pathogen substance are PR proteins (PRPs described in EP-A-0392225), and the like. These anti-pathogen substances and genetically engineered crop plants which produce such anti-pathogen substances are described in EP-A-0392225, WO 95/33818, EP-A-0353191, and the like. Examples of the anti-pathogen substances expressed in the genetically engineered crop plants include ion channel inhibitors such as sodium channel inhibitors and calcium channel inhibitors (KP1, KP4, KP6 toxins produced by viruses are known); stilbene synthase; bibenzyl synthase; chitinase; glucanase; PR proteins; and anti-pathogen substances produced by microorganisms, such as peptide antibiotics, heterocycle-containing antibiotics, and protein factors involved in plant disease-resistance (referred to as plant disease resistance genes and described in WO 03/000906).

The above-described crop plants include those to which a beneficial character such as a modified oil component or an enhanced amino acid content has been imparted by a genetic engineering technique. Examples of such crop plants include VISTIVE (registered trademark) (low linolenic soybean which has a reduced content of linolenic acid), and high-lysine (high-oil) corn (corn which has an increased content of lysine or oil).

Furthermore, the above-described crop plants include stacked plants which have a combination of two or more of beneficial characters such as the above-described classical herbicide-resistant character, or a herbicide-resistance gene, an insecticidal pest-resistant gene, an anti-pathogen substance-producing gene, a modified oil component, and an enhanced amino acid content.

The neonicotinoideneonicotinoid compound of the present invention includes clothianidin, thiamethoxam, imidacloprid, dinotefuran, nitenpyram, acetamiprid, and thiacloprid.

In the step of treating a soybean seed or a corn seed with the neonicotinoideneonicotinoid compound, such a neonicotinoid compound is usually mixed with a solid carrier or a liquid carrier, formulated with optional addition of an auxiliary agent for formulation, such as surfactants, and then used.

The dosage of the neonicotinoideneonicotinoid compound used for treating soybean or corn seeds is usually in the range of 0.001 to 40 g per 1 kg of seeds, preferably 0.01 to 10 g per 1 kg of seeds. The method for applying an active ingredient to plant seeds includes, for example, a method of subjecting a seed to dust coating with a formulation containing an active ingredient, a method of immersing a seed in a formulation containing an active ingredient, and a method of coating a seed with a carrier containing an active ingredient.

(2) The step of treating the field with at least one PPO inhibitor compound selected from the group consisting of flumioxazin, sulfentrazone, saflufenacil, oxyfluorfen, and 3-(4-chloro-6-fluoro-2-trifluoromethylbenzimidazol-7-yl)-1-methyl-6-trifluoromethyl-2,4-(1H,3H)pyrimidinedione before or after the soybean or corn seeds treated with the neonicotinoideneonicotinoid compound are sown in the field The PPO inhibitor compound is a herbicidal compound which inhibits protoporphillinogen IX oxidase (EC1.3.3.4) located on a chlorophyll synthesis pathway in plant plastids, thereby causing withering and death of the plant.

The PPO inhibitor compound of the present invention includes flumioxazin, sulfentrazone, saflufenacil, oxyfluorfen, and 3-(4-chloro-6-fluoro-2-trifluoromethylbenzimidazol-7-yl)-1-methyl-6-trifluoromethyl-2,4-(1H,3H)pyrimidinedione.

In the step of treating a field with the PPO inhibitor compound, such a PPO inhibitor compound is usually mixed with a solid carrier or a liquid carrier, formulated with optional addition of an auxiliary agent for formulation, such as surfactants, and then used.

Examples of the method of treating a field with a PPO inhibitor compound include a method of scatteringapplying a PPO inhibitor compound in the soil of the field, and a method of applyingscattering a PPO inhibitor compound on weeds after their germination.

The dosage of the PPO inhibitor compound used for treating the field is usually 5 to 500 g per 10,000 m$^2$. In the step of treating the field with the PPO inhibitor compound, an adjuvant may be mixed at the time of such treatment with the PPO inhibitor compound.

The soybean or corn seeds which have been treated with the neonicotinoideneonicotinoid compound are sown in a field by a conventional method. In the method for controlling noxious organisms according to the present invention, the PPO inhibitor compound may be applied before sowing soybean or corn seeds, or may be applied after sowing soybean or corn seeds.

In the case where the PPO inhibitor compound is applied before sowing soybean or corn seeds, the PPO inhibitor compound is applied 50 days before to immediately before the sowing, preferably 30 days before to immediately before the sowing, more preferably 20 days before to immediately before the sowing.

In the case where the PPO inhibitor compound is applied after sowing soybean or corn seeds, the PPO inhibitor compound is applied immediately after to 50 days after the sowing, preferably immediately after to 3 days after the sowing. Concrete treatment time in the treatment with the PPO inhibitor compound after sowing soybean seeds includes, for example, the time from pre-emergence of soybean to flowering time. The time from pre-emergence of soybean to flowering time is preferably the time from pre-emergence of soybean to a stage of 6 compound leaves, and more preferably the time from pre-emergence of soybean to a stage of 3 compound leaves. Concrete treatment time in the treatment with the PPO inhibitor compound after sowing corn seeds includes the time from pre-emergence of corn to 12 leaf stage, preferably the time from pre-emergence of corn to 8 leaf stage, and more preferably the time from pre-emergence of corn to 6 leaf stage. The leaf age of corn is determined by the leaf collar method.

According to the method for controlling noxious organisms of the present invention, noxious organisms such as harmful arthropods and weeds in the fields of soybean or corn can be controlled.

Examples of such harmful arthropods include the followings.

Hemipteran pests: planthoppers such as *Laodelphax striatellus*, *Nilaparvata lugens*, and *Sogatella furcifera*, leafhoppers such as *Nephotettix cincticeps*, and *Nephotettix virescens*, aphids such as *Aphis gossypii*, *Myzus persicae*, *Brevicoryne brassicae*, *Macrosiphum euphorbiae*, *Aulacorthum solani*, *Rhopalosiphum padi*, and *Toxoptera citricidus*, plant bugs such as *Nezara antennata*, *Riptortus clavetus*, *Leptocorisa chinensis*, *Eysarcoris parvus*, *Halyomorpha mista*, and *Lygus lineolaris*, whiteflies such as *Trialeurodes vaporariorum*, *Bemisia tabaci*, and *Bemisia argentifolii*, scales such as *Aonidiella aurantii*, *Comstockaspis perniciosa*, *Unaspis citri*, *Ceroplastes rubens*, and *Icerya purchasi*, lace bugs, jumping plantlices, and the like;

Lepidopteran pests: Pyralidae such as *Chilo suppressalis*, *Tryporyza incertulas*, *Cnaphalocrocis medinalis*, *Notarcha derogata*, *Plodia interpunctella*, *Ostrinia furnacalis*, *Ostrinia nubilaris*, *Hellula undalis*, and *Pediasia teterrellus*, Noctuidae such as *Spodoptera litura*, *Spodoptera exigua*, *Pseudaletia separata*, *Mamestra brassicae*, *Agrotis ipsilon*, *Plusia nigrisigna*, *Trichoplusia* spp., *Heliothis* spp., and *Helicoverpa* spp., Pieridae such as *Pieris rapae*, *Adoxophyes* spp., Tortricidae such as *Grapholita molesta*, *Leguminivora glycinivorella*, *Matsumuraeses azukivora*, *Adoxophyes orana fasciata*, *Adoxophyes* sp., *Homona magnanima*, *Archips fuscocupreanus*, and *Cydia pomonella*, Gracillariidae such as *Caloptilia theivora*, and *Phyllonorycter ringoneella*, Carposimidae such as *Carposina niponensis*, Lyonetiidae such as *Lyonetia* spp., Lymantriidae spp., Lymantriidae such as *Euproctis* spp., Yponameutidae such as *Plutella xylostella*, Gelechiidae such as *Pectinophora gossypiella*, and *Phthorimaea operculella*, Arctiidae such as *Hyphantria cunea*, Tineidae such as *Tinea translucens*, and *Tineola bisselliella*, and the like;

Thysanopteran pests: Thripidae such as *Frankliniella occidentalis*, *Thrips parmi*, *Scirtothrips dorsalis*, *Thrips tabaci*, *Frankliniella intonsa*, and *Frankliniella fusca*, and the like;

Dipteran pests: Agromyzidae such as *Musca domestica*, *Culex popiens pallens*, *Tabanus trigonus*, *Hylemya antiqua*, *Hylemya platura*, *Anopheles sinensis*, *Agromyza oryzae*, *Hydrellia griseola*, *Chlorops oryzae*, and *Liriomyza trifolii*, *Dacus cucurbitae*, *Ceratitis capitata*, and the like;

Coleopteran pest: *Epilachna vigintioctopunctata*, *Aulacophora femoralis*, *Phyllotreta striolata*, *Oulema oryzae*, *Echinocnemus squameus*, *Lissorhoptrus oryzophilus*, *Anthonomus grandis*, *Callosobruchus chinensis*, *Sphenophorus venatus*, *Popillia japonica*, *Anomala cuprea*, *Diabrotica* spp., *Leptinotarsa decemlineata*, *Agriotes* spp., *Lasioderma serricorne*, *Anthrenus verbasci*, *Tribolium castaneum*, *Lyctus brunneus*, *Anoplophora malasiaca*, *Tomicus piniperda*, and the like;

Orthopteran pests: *Locusta migratoria*, *Gryllotalpa africana*, *Oxya yezoensis*, *Oxya japonica*, and the like;

Hymenopteran pests: *Athalia rosae*, *Acromyrmex* spp., *Solenopsis* spp., and the like;

Blattaria pests: *Blattella germanica*, *Periplaneta fuliginosa*, *Periplaneta americana*, *Periplaneta brunnea*, *Blatta orientalis*, and the like;

Acarina pests: Tetranychidae such as *Tetranychus urticae*, *Panonychus citri*, and *Oligonychus* spp., Eriophyidae such as *Aculops pelekassi*, Tarsonemidae such as *Polyphagotarsonemus latus*, Tenuipalpidae, Tuckerellidae, Acaridae such as *Tyrophagus putrescentiae*, Dermanyssidae such as *Dermatophagoides farinae*, and *Dermatophagoides ptrenyssnus*, Cheyletidae such as *Cheyletus eruditus*, *Cheyletus malaccensis*, and *Cheyletus moorei*, and the like.

Examples of such weeds include the followings. Polygonaceae weeds: *Polygonum convolvulus*, *Polygonum lapathifolium*, *Polygonum pensylvanicum*, *Polygonum persicaria*, *Polygonum longisetum*, *Polygonum aviculare*, *Polygonum arenastrum*, *Polygonum cuspidatum*, *Rumex japonicus*, *Rumex crispus*, *Rumex obtusifolius*, *Rumex acetosa*, Portulaceae seeds: *Portulaca oleracea*, Caryophyllaceae weeds: *Stellaria media*, *Cerastium holosteoides*, *Cerastium glomeratum*, *Spergula arvensis*, Chenopodiaceae weeds: *Chenopodium album*, *Kochia scoparia*, *Salsola kali*, *Atriplex* spp., Amaranthaceae weeds: *Amaranthus retroflexus*, *Amaranthus viridis*, *Amaranthus lividus*, *Amaranthus spinosus*, *Amaranthus hybridus*, *Amaranthus palmeri*, *Amaranthus rudis*, *Amaranthus patulus*, *Amaranthus tuberculatos*, *Amaranthus blitoides*, *Alternanthera philoxeroides*, *Alternanthera sessilis*, Papaveraceae weeds: *Papaver rhoeas*, Cruciferae weeds: *Raphanus raphanistrum*, *Sinapis arvensis*, *Capsella bursa-pastoris*, *Brassica juncea*, *Descurainia pinnata*, *Rorippa islandica*, *Rorippa sylvestris*, *Thlaspi arvense*, Leguminosae weeds: *Aeschynomene indica*, *Sesbania exaltata*, *Cassia obtusifolia*, *Cassia occidentalis*, *Desmodium tortuosum*, *Trifolium repens*, *Pueraria lobata*, *Vicia angustifolia*, Oxalidaceae weeds: *Oxalis corniculata*, *Oxalis strica*, Geraniaceae weeds: *Geranium carolinense*, *Erodium cicutarium*, Euphorbiaceae weeds: *Euphorbia helioscopia*, *Euphorbia maculata*, *Euphorbia humistrata*, *Euphorbia esula*, *Euphorbia heterophylla*, *Acalypha australis*, Malvaceae weeds: *Abutilon theophrasti*, *Sida spinosa*, *Hibiscus trionum*, Violaceae weeds: *Viola arvensis*, *Viola tricolor*, Cucurbitaceae weeds: *Sicyos angulatus*, *Echinocystis lobata*, Lythraceae weeds: *Lythrum salicaria*, Apiaceae weeds: *Hydrocotyle sibthorpioides*, Asclepiadaceae weeds: *Asclepias syriaca*, *Ampelamus albidus*

Rubiaceae weeds: *Galium aparine*, *Galium spurium* var. *echinospermon*, *Spermacoce latifolia*, Convolvulaceae weeds: *Ipomoea nil*, *Ipomoea hederacea*, *Ipomoea purpurea*, *Ipomoea hederacea* var. *integriuscula*, *Ipomoea lacunosa*, *Ipomoea triloba*, *Ipomoea coccinea*, *Ipomoea quamoclit*, *Convolvulus arvensis*, *Calystegia hederacea*, Boraginaceae weeds: *Myosotis arvensis*, Lamiaceae weeds: *Lamium purpureum*, *Lamium amplexicaule*, Solanaceae weeds: *Datura stramonium*, *Solanum nigrum*, *Solanum americanum*, *Solanum ptycanthum*, *Solanum sarrachoides*, *Solanum rostratum*, *Solanum aculeatissimum*, *Solanum carolinense*, *Physalis angulata*, *Physalis subglabrata*, *Nicandra physaloides*, Scrophulariaceae weeds: *Veronica hederaefolia*, *Veronica persica*, *Veronica arvensis*, Plantaginaceae weeds: *Plantago asiatica*, Compositae weeds: *Xanthium pensylvanicum*, *Xanthium occidentale*, *Helianthus annuus*, *Matricaria chamomilla*, *Matricaria perforata*, *Chrysanthemum segetum*, *Matricaria matricarioides*, *Artemisia princeps*, *Solidago altissima*, *Taraxacum officinale*, *Galinsoga ciliata*, *Senecio vulgaris*, *Conyza bonariensis*, *Conyza canadensis*, *Ambrosia artemisiaefolia*, *Ambrosia trifida*, *Bidens pilosa*, *Bidens frondosa*, *Cirsium arvense*, *Cirsium vulgare*, *Carduus nutans*, *Lactuca serriola*, *Sonchus asper*, Liliaceae weeds: *Allium canadense*, *Allium vineale*, Commelinaceae weeds: *Commelina communis*, *Commelina bengharensis*, Poaceae weeds: *Echinochloa crus-galli*, *Setaria viridis*, *Setaria faberi*, *Setaria glauca*, *Digitaria ciliaris*, *Digitaria sanguinalis*, *Eleusine indica*, *Poa annua*, *Alospecurus aequalis*, *Alopecurus myosuroides*, *Avena fatua*, *Sorghum halepense*, *Sorghum vulgare*, *Agropyron repens*, *Lolium mul-*

*tiflorum, Lolium perenne, Lolium rigidum, Bromus secalinus, Bromus tectorum, Hordeum jubatum, Aegilops cylindrica, Phalaris arundinacea, Phalaris minor, Apera spica-venti, Panicum dichotomiflorum, Panicum texanum, Brachiaria platyphylla, Cenchrus echinatus, Cenchrus pauciflorus, Eriochloa villosa,*
Cyperaceae weeds: *Cyperus microiria, Cyperus iria, Cyperus rotundus, Cyperus esculentus, Kyllinga gracillima,* Equisetaceae weeds: *Equisetum arvense, Equisetum palustre,* and the like.

In the method for controlling noxious organisms according to the present invention, one or more other agricultural chemicals may be used in combination. Such other agricultural chemicals include, for example, insecticides, acaricides, nematicides, fungicides, herbicides, plant growth regulators, and safeners.

Examples of such other agricultural chemicals include the followings.

Insecticides: fenthion, fenitrothion, pirimiphos-methyl, diazinon, quinalphos, isoxathion, Pyridafenthion, chlorpyrifos-methyl, vamidothion, malathion, phenthoate, dimethoate, disulfoton, monocrotophos, tetrachlorvinphos, chlorfenvinphos, propaphos, acephate, trichlorphon, EPN, pyraclorfos, carbaryl, metolcarb, isoprocarb, BPMC, propoxur, XMC, carbofuran, carbosulfan, benfuracarb, furathiocarb, methomyl, thiodicarb, cycloprothrin, ethofenprox, cartap, bensultap, thiocyclam, buprofezin, tebufenozide, ethiprole, and pyridalyl.

Acaricides: hexythiazox, pyridaben, fenpyroximate, tebufenpyrad, chlorfenapyr, etoxazole, pyrimidifen, and spirodiclofen.

Nematicides: fosthiazate.

Fungicides: captan, IBP, EDDP, tolclofos-methyl, benomyl, carbendazim, thiophanate-methyl, mepronil, flutolanil, thifluzamid, furametpyr, teclofthalam, pencycuron, carpropamid, diclocymet, metalaxyl, triflumizole, azaconazole, bromuconazole, cyproconazole, diclobutrazol, difenoconazole, diniconazole, Mdiniconazole-M, epoxiconazole, fenbuconazole, fluquinconazole, flusilazole, flutriafol, furconazole, furconazole-cis, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole, pefurazoate, prochloraz, azoxystrobin, dimoxystrobin, fluoxastrobin, kresoxim-methyl, metominostrobin, orysastrobin, picoxystrobin, pyraclostrobin, trifloxystrobin, validamycinA, blasticidin S, kasugamycin, polyoxin, fthalide, probenazole, isoprothiolane, tricyclazole, pyroquilon, ferimzone, acibnzolar S-methyl, diclomezine, oxolinic acid, phenazine oxide, TPN, and iprodione.

Herbicides: dicamba, 2,4-D, 2,4-DB, MCPA, MCPB, mecoprop, Pmecoprop-P, dichlorprop, Pdichlorprop-P, bromoxynil, dichlobenil, ioxynil, di-allate, butylate, tri-allate, phenmedipham, chlorpropham, asulam, phenisopham, benthiocarb, molinate, esprocarb, pyributicarb, prosulfocarb, orbencarb, EPTC, dimepiperate, swep, propachlor, metazachlor, alachlor, acetochlor, metolachlor, S-metolachlor, butachlor, pretilachlor, thenylchlor, aminocyclopyrachlor, trifluralin, pendimethalin, ethalfluralin, benfluralin, prodiamine, simazine, atrazine, propazine, cyanazine, ametryn, simetryn, dimethmetryn, prometryn, indaziflam, triaziflam, metribuzin, hexazinone, isoxaben, diflufenican, diuron, linuron, fluometuron, difenoxuron, methyl-daimuron, isoproturon, isouron, tebuthiuron, benzthiazuron, methabenzthiazuron, propanil, mefenacet, clomeprop, napropanilide, bromobutide, daimuron, cumyluron, diflufenzopyr, etobenzanid, bentazon, tridiphane, indanofan, amitrole, fenchiorazole, clomazone, maleic hydrazide, pyridate, chloridazon, norflurazon, bromacil, terbacil, oxaziclomefone, cinmethylin, benfuresate, cafenstrole, pyrithiobac, pyrithiobac-sodium, pyriminobac, pyriminobac-methyl, bispyribac, bispyribac-sodium, pyribenzoxim, pyrimisulfan, pyriftalid, fentrazamide, dimethenamid, dimethenamid-P, ACN, benzobicyclon, dithiopyr, triclopyr, thiazopyr, aminopyralid, clopyralid, dalapon, chlorthiamid, amidosulfuron, azimsulfuron, bensulfuron, bensulfuron-methyl, chlorimuron, chlorimuron-ethyl, cyclosulfamuron, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, mesosulfuron, mesosulfuron-methyl, nicosulfuron, orthosulfamuron, oxasulfuron, primisulfuron, primisulfuron-methyl, propyrisulfuron, pyrazosulfuron, pyrazosulfuron-ethyl, rimsulfuron, sulfometuron, sulfometuron-methyl, sulfosulfuron, trifloxysulfuron, chlorsulfuron, cinosulfuron, ethametsulfuron, ethametsulfuron-methyl, iodosulfuron, iodosulfuron-methyl-sodium, metsulfuron, metsulfuron-methyl, prosulfuron, thifensulfuron, thifensulfuron-methyl, triasulfuron, tribenuron, tribenuron-methyl, triflusulfuron, triflusulfuron-methyl, tritosulfuron, picolinafen, beflubutamid, mesotrione, sulcotrione, tefuryltrione, tembotrione, isoxachlortole, isoxaflutole, benzofenap, pyrasulfotole, pyrazolynate, pyrazoxyfen, topramezone, flupoxam, amicarbazone, bencarbazone, flucarbazone, flucarbazone-sodium, ipfencarbazone, propoxycarbazone, propoxycarbazone-sodium, thiencarbazone, thiencarbazone-methyl, cloransulam, cloransulam-methyl, diclosulam, florasulam, flumetsulam, metosulam, penoxsulam, pyroxsulam, imazamethabenz, imazamethabenz-methyl, imazamox, imazamox-ammonium, imazapic, imazapic-ammonium, imazapyr, imazaquin, imazethapyr, clodinafop, clodinafop-propargyl, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, propaquizafop, quizalofop, quizalofop-ethyl, quizalofop-P, quizalofop-P-ethyl, alloxydim, clethodim, sethoxydim, tepraloxydim, tralkoxydim, pinoxaden, pyroxasulfone, glyphosate, glyphosate-isopropylamine, glyphosate-trimethylsulfonium, glyphosate-ammonium, glyphosate-diammonium, glyphosate-sodium, glyphosate-potassium, glufosinate, glufosinate-ammonium, glufosinate-P, glufosinate-P-sodium, bialafos, anilofos, bensulide, butamifos, paraquat, and diquat.

Plant growth regulators: hymexazol, paclobutrazol, uniconazole, uniconazole-P, inabenfide, prohexadione-calcium, 1-methylcyclopropene, trinexapac, and gibberellins. Safeners: benoxacor, cloquintocet, cyometrinil, cyprosulfamide, dichlormid, dicyclonon, diethotate, fenchlorazole, fenclorim, flurazole, fluxofenim, furilazole, isoxadifen, mefenpyr, mephenate, naphthalic anhydride, and oxabetrinil.

EXAMPLES

The present invention will be illustrated by the following examples, but the present invention is not limited to these examples. In addition, ha in the following descriptions means hectare, i.e. 10,000 m$^2$.

First of all, evaluation criteria for an insecticidal effect, a herbicidal effect, and phytotoxicity described in the following examples are shown.

[Insecticidal Effect]

The evaluation of the insecticidal effect was performed by determining the life and death of the insects at the time of the investigation and calculating the protective value according to the following equation;

Protective Value(%)=100×(1−T/C)

wherein the symbols have the following meanings;

C: The number of insects at the time of observation in an untreated section: and T: The number of insects at the time of observation in a treated section.

[Herbicidal Effect and Phytotoxicity]

The herbicidal effect is evaluated using a scale of 0 to 100, wherein a score of "0" means that there is no or little difference in the degree of germination or growth in test weeds between treated weeds and untreated weeds at the time of observation, and a score of "100" means that the test weeds result in complete withering and death or their germination or growth is completely inhibited.

The phytotoxicity against crop plants is evaluated by using "no harm", "low", "moderate" or "high", wherein "no harm" means that no or little phytotoxicity is found, "low" means that a slight degree of phytotoxicity is found, "moderate" means that a medium degree of phytotoxicity is found, and "high" means that a severe degree of phytotoxicity is found. The "phytotoxicity" herein evaluated means the symptoms of injury which have been judged to be attributable to the compound being applied, not the symptoms of injury caused by pests, and this difference should be clearly distinguished.

Example 1

In a plastic cup of 96 mm in inside diameter and 44 mm in height, 24.5 μL of a clothianidin suspension (a suspension containing 20% of clothianidin, trade name: Dantotsu Flowable, manufactured by Sumitomo Chemical Co., Ltd.) and 50 soybean seeds were placed. The plastic cup was shaken by the hand so that the clothianidin suspension was attached to the soybean seeds.

A soil in admixture with about 500 mg each of the seeds of *Portulaca oleracea*, *Amaranthus retroflexus*, and *Polygonum lapathifolium* was packed in a plastic pot of 177 mm in inside diameter and 140 mm in height. The above soybean seeds were sown in this pot at a rate of two seeds per pot. On the day of sowing soybean seeds and after the sowing, an aqueous diluted solution (55.8 ppm or 111.6 ppm) of a flumioxazin water dispersible granule (a wettable granulea water dispersible granule containing 51% of flumioxazin, trade name: Valor SX, manufactured by Valent, USAValent USA Corp.) was uniformly sprayed on the soil surface with a sprayer so as to apply the dosage given in the table.

Thereafter, the test pot was placed in a greenhouse. On day 15 after soybean sowing, 20 larvae and imagos of *Aulacorthum solani* alive on a soybean leaf were placed in the pot and the whole plant was covered with a nylon cloth.

On day 6 after release of *Aulacorthum solani*, the insecticidal effect, herbicidal effect, and phytotoxicity were examined. The insecticidal effect is shown in Table 1 and the herbicidal effect and phytotoxicity are shown in Table 2.

TABLE 1

| Clothianidin Treatment | Flumioxazin Treatment | Protective Value |
|---|---|---|
| None | 12.5 g/ha | 0 |
| None | 25 g/ha | 0 |

TABLE 1-continued

| Clothianidin Treatment | Flumioxazin Treatment | Protective Value |
|---|---|---|
| 44.7 g/ha | None | 59.1 |
| 44.7 g/ha | 12.5 g/ha | 76.4 |
| 44.7 g/ha | 25 g/ha | 71.2 |

TABLE 2

| Clothianidin Treatment | Flumioxazin Treatment | Evaluation of Effect on Weeds | Phytotoxicity to Soybean |
|---|---|---|---|
| 44.7 g/ha | 12.5 g/ha | 100 | No harm |
| 44.7 g/ha | 25 g/ha | 100 | No harm |

Example 2

In a plastic cup of 96 mm in inside diameter and 44 mm in height, 31.4 μL of a thiamethoxam formulation (a formulation containing 30% of thiamethoxam, trade name: CRUISER FS30, manufactured by Syngenta Japan KK) and 50 soybean seeds were placed. The plastic cup was shaken by the hand so that the thiamethoxam formulation was attached to the soybean seeds.

A soil in admixture with about 500 mg each of the seeds of *Portulaca oleracea*, *Amaranthus retroflexus*, and *Polygonum lapathifolium* was packed in a plastic pot of 177 mm in inside diameter and 140 mm in height. The above soybean seeds were sown in this pot at a rate of two seeds per pot. On the day of sowing soybean seeds and after the sowing, an aqueous diluted solution (223.2 ppm) of a flumioxazin water dispersible granule (a wettable granulea water dispersible granule containing 51% of flumioxazin, trade name: Valor SX, manufactured by Valent, USAValent USA Corp.) was uniformly sprayed on the soil surface with a sprayer so as to apply the dosage given in the table.

Thereafter, the test pot was placed in a greenhouse. On day 15 after soybean sowing, 20 larvae and imagos of *Aulacorthum solani* alive on a soybean leaf were placed in the pot and the whole pot was covered with a nylon cloth.

On day 6 after release of *Aulacorthum solani*, the insecticidal effect, herbicidal effect, and phytotoxicity were investigated. The insecticidal effect is shown in Table 3 and the herbicidal effect and phytotoxicity are shown in Table 4.

TABLE 3

| Thiamethoxam Treatment | Flumioxazin Treatment | Protective Value |
|---|---|---|
| None | 50 g/ha | 0 |
| 78.9 g/ha | None | 86.9 |
| 78.9 g/ha | 50 g/ha | 100 |

TABLE 4

| Thiamethoxam Treatment | Flumioxazin Treatment | Evaluation of Effect on Weeds | Phytotoxicity to Soybean |
|---|---|---|---|
| 78.9 g/ha | 50 g/ha | 100 | No harm |

Example 3

In a plastic cup of 96 mm in inside diameter and 44 mm in height, 16.0 μl, of a clothianidin suspension (a suspension containing 20% of clothianidin, trade name: Dantotsu Flowable, manufactured by Sumitomo Chemical Co. Ltd.) and 50 soybean seeds were placed. The plastic cup was shaken by the hand so that the clothianidin suspension was attached to the soybean seeds.

A soil in admixture with about 500 mg each of the seeds of *Spergula arvensis*, *Portulaca oleracea*, and *Amaranthus retroflexus* was packed in a plastic pot of 177 mm in inside diameter and 140 mm in height. The above soybean seeds were sown in this pot at a rate of two seeds per pot. On the day of sowing soybean seeds and after the sowing, an aqueous diluted solution (892.9 ppm) of a sulfentrazone dry flowable formulation (a dry flowable formulation containing 75% of sulfentrazone, trade name: Cover 75 DF, manufactured by Du Pont Kabushiki Kaisha) was uniformly sprayed on the soil surface with a sprayer so as to apply the dosage given in the table.

Thereafter, the test pot was placed in a greenhouse. On day 14 after soybean sowing, 20 larvae and imagos of *Aulacorthum solani* alive on a soybean leaf were placed in the pot and the whole pot was covered with a nylon cloth.

On day 7 after release of *Aulacorthum solani*, the insecticidal effect, herbicidal effect, and phytotoxicity were examined. The insecticidal effect is shown in Table 5 and the herbicidal effect and phytotoxicity are shown in Table 6.

TABLE 5

| Clothianidin Treatment | Sulfentrazone Treatment | Protective Value |
|---|---|---|
| None | 200 g/ha | 0 |
| 55.3 g/ha | None | 55.2 |
| 55.3 g/ha | 200 g/ha | 88.7 |

TABLE 6

| Clothianidin Treatment | Sulfentrazone Treatment | Evaluation of Effect on Weeds | Phytotoxicity to Soybean |
|---|---|---|---|
| 55.3 g/ha | 200 g/ha | 100 | No harm |

Example 4

In a plastic cup of 96 mm in inside diameter and 44 mm in height, 108.8 μL of a clothianidin suspension (a suspension containing 20% of clothianidin, trade name: Dantotsu Flowable, manufactured by Sumitomo Chemical Co., Ltd.) and 30 corn seeds were placed. The plastic cup was shaken by the hand so that the clothianidin suspension was attached to the corn seeds. In addition, the clothianidin suspension was attached to the corn seeds in a similar manner except that it was used in an amount of 217.5 μL.

A soil in admixture with about 500 mg each of the seeds of *Spergula arvensis*, *Portulaca oleracea*, and *Amaranthus retroflexus* was packed in a plastic pot of 177 mm in inside diameter and 140 mm in height. The above corn seeds were sown in this pot at a rate of two seeds per pot. On the day of sowing corn seeds and after the sowing, an aqueous diluted solution (66.6 ppm or 223.2 ppm) of a flumioxazin water dispersible granule (a wettable granulea water dispersible granule containing 51% of flumioxazin, trade name: Valor SX, manufactured by Valent, USAValent USA Corp.) was uniformly sprayed on the soil surface with a sprayer so as to apply the dosage given in the table.

Thereafter, the test pot was placed in a greenhouse. On day 22 after corn sowing, 10 fourth-instar larvae of *Spodoptera litura* were released in the pot and the whole pot was then covered with a nylon cloth.

On day 3 after release of *Spodoptera litura*, the insecticidal effect was examined.

In addition, on day 22 after corn sowing, the herbicidal effect and phytotoxicity were examined.

The insecticidal effect is shown in Table 7, and the herbicidal effect and phytotoxicity are shown in Table 8.

TABLE 7

| Clothianidin Treatment | Flumioxazin Treatment | Protective Value |
|---|---|---|
| None | 12.5 g/ha | 0 |
| None | 50 g/ha | 5 |
| 553 g/ha | None | 30 |
| 984 g/ha | None | 65 |
| 553 g/ha | 12.5 g/ha | 100 |
| 553 g/ha | 50 g/ha | 100 |
| 984 g/ha | 12.5 g/ha | 100 |
| 984 g/ha | 50 g/ha | 100 |

TABLE 8

| Clothianidin Treatment | Flumioxazin Treatment | Evaluation of Effect on Weeds | Phytotoxicity to Corn |
|---|---|---|---|
| 553 g/ha | 12.5 g/ha | 100 | No harm |
| 553 g/ha | 50 g/ha | 100 | No harm |
| 984 g/ha | 12.5 g/ha | 100 | No harm |
| 984 g/ha | 50 g/ha | 100 | No harm |

Example 5

In a plastic cup of 96 mm in inside diameter and 44 mm in height, 108.8 μL of a clothianidin suspension (a suspension containing 20% of clothianidin, trade name: Dantotsu Flowable, manufactured by Sumitomo Chemical Co., Ltd.) and 30 corn seeds were placed. The plastic cup was shaken by the hand so that the clothianidin suspension was attached to the corn seeds. In addition, the clothianidin suspension was attached to the corn seeds in a similar manner except that it was used in an amount of 217.5 μL.

A soil in admixture with about 500 mg each of the seeds of *Polygonum lapathifolium, Amaranthus retroflexus*, and *Portulaca oleracea* was packed in a plastic pot of 177 mm in inside diameter and 140 mm in height. The above corn seeds were sown in this pot at a rate of one seed per pot. On the day of sowing corn seeds and after the sowing, an aqueous diluted solution (64 ppm or 250 ppm) of saflufenacil was uniformly sprayed on the soil surface with a sprayer so as to apply the dosage given in the table. The aqueous diluted solution of saflufenacil was prepared by dissolving a given amount of saflufenacil in acetone containing 2% (w/v) of Tween 20, and diluting this solution with water to an acetone concentration of 10% (v/v).

Thereafter, the test pot was placed in a greenhouse. On day 22 after corn sowing, 10 fourth-instar larvae of *Spodoptera litura* were released in the pot and the whole pot was then covered with a nylon cloth.

On day 3 after release of *Spodoptera litura*, the insecticidal effect was examined.

In addition, on day 22 after corn sowing, the herbicidal effect and phytotoxicity were examined.

The insecticidal effect is shown in Table 9, and the herbicidal effect and phytotoxicity are shown in Table 10.

TABLE 9

| Clothianidin Treatment | Saflufenacil Treatment | Protective Value |
| --- | --- | --- |
| None | 32 g/ha | 0 |
| None | 125 g/ha | 0 |
| 272 g/ha | None | 30 |
| 496 g/ha | None | 40 |
| 272 g/ha | 32 g/ha | 80 |
| 272 g/ha | 125 g/ha | 100 |
| 496 g/ha | 32 g/ha | 90 |
| 496 g/ha | 125 g/ha | 100 |

TABLE 10

| Clothianidin Treatment | Saflufenacil Treatment | Evaluation of Effect on Weeds | Phytotoxicity to Corn |
| --- | --- | --- | --- |
| 272 g/ha | 32 g/ha | 100 | No harm |
| 272 g/ha | 125 g/ha | 100 | No harm |
| 496 g/ha | 32 g/ha | 100 | No harm |
| 496 g/ha | 125 g/ha | 100 | No harm |

Example 6

In a plastic cup of 96 mm in inside diameter and 44 mm in height, 11.1 μl of a clothianidin suspension (a suspension containing 20% of clothianidin, trade name: Dantotsu Flowable, manufactured by Sumitomo Chemical Co., Ltd.) and 20 soybean seeds were placed. The plastic cup was shaken by the hand so that the clothianidin suspension was attached to the soybean seeds.

A soil was packed in a 1/5000a Wagner pot. The above soybean seeds were sown in the Wagner pot at a rate of two seeds per pot, and the seeds of *Ipomoea hederacea* were sown in the pot at a rate of three seeds per pot. On the day of sowing soybean seeds and after the sowing, a flumioxazin granule (a granule containing 0.25% of flumioxazin, trade name: BroadStar, manufactured by Valent, USAValent USA Corp.) were uniformly scattered on the soil surface by the hand so as to apply the dosage given in Table 11.

On day 11 after sowing of the seeds of soybean and *Ipomoea hederacea*, the herbicidal effect and phytotoxicity were examined.

The herbicidal effect and phytotoxicity are shown in Table 11.

TABLE 11

| Clothianidin Treatment | Flumioxazin Treatment | Evaluation of Effect on Weeds | Phytotoxicity to Soybean |
| --- | --- | --- | --- |
| 73 g/ha | None | 0 | No harm |
| None | 25 g/ha | 25 | No harm |
| 73 g/ha | 25 g/ha | 85 | No harm |

Example 7

In a plastic cup of 96 mm in inside diameter and 44 mm in height, 108.75 μL of a clothianidin suspension (a suspension containing 20% of clothianidin, trade name: Dantotsu Flowable, manufactured by Sumitomo Chemical Co., Ltd.) and 30 corn seeds were placed. The plastic cup was shaken by the hand so as to attach the clothianidin suspension to the corn seeds.

A soil was packed in a 1/5000a Wagner pot. The above corn seeds were sown in the Wagner pot at a rate of one seed per pot, and the seeds of *Ipomoea hederacea* were sown in the pot at a rate of three seeds per pot. On the day of sowing corn seeds and after the sowing, an aqueous diluted solution (100 ppm) of saflufenacil was uniformly drenched on the soil surface with a pipette so as to apply the dosage given in the table. The aqueous diluted solution of saflufenacil was prepared by dissolving a given amount of saflufenacil in acetone containing 2% (w/v) of Tween 20, and diluting this solution with water to an acetone concentration of 10% (v/v).

On day 11 after sowing of the seeds of corn and *Ipomoea hederacea*, the herbicidal effect and phytotoxicity were examined.

The herbicidal effect and phytotoxicity are shown in Table 12.

TABLE 12

| Clothianidin Treatment | Saflufenacil Treatment | Evaluation of Effect on Weeds | Phytotoxicity to SoybeanCorn |
| --- | --- | --- | --- |
| 340 g/ha | None | 0 | No harm |
| 605 g/ha | None | 0 | No harm |
| None | 32 g/ha | 50 | No harm |
| 340 g/ha | 32 g/ha | 100 | No harm |
| 605 g/ha | 32 g/ha | 100 | No harm |

Example 8

Clothianidin is attached to soybean seeds and corn seeds. Then, a soil is packed in a pot, and the above seeds and weed seeds are sown. On the day of sowing, 3-(4-chloro-6-fluoro-2-trifluoromethylbenzimidazol-7-yl)-1-methyl-6-trifluoromethyl-2,4-(1H,3H)pyrimidinedione is uniformly applied to the soil surface. The pot is placed in a greenhouse.

On day 10 after sowing, the herbicidal effect against the weeds is examined. As a result, a control effect against the weeds can be confirmed.

Example 9

Clothianidin is attached to soybean seeds and corn seeds. Then, a soil is packed in a pot, and the above seeds and weed seeds are sown. On the day of sowing, oxyfluorfen is uniformly applied to the soil surface. The pot is placed in a greenhouse.

On day 10 after sowing, the herbicidal effect against the weeds is examined. As a result, a control effect against the weeds can be confirmed.

Example 10

Thiamethoxam is attached to soybean seeds and corn seeds. Then, a soil is packed in a pot, and the above seeds and weed seeds are sown. On the day of sowing, 3-(4-chloro-6-fluoro-2-trifluoromethylbenzimidazol-7-yl)-1-methyl-6-trifluoromethyl-2,4-(1H,3H)pyrimidinedione is uniformly applied to the soil surface. The pot is placed in a greenhouse.

On day 10 after sowing, the herbicidal effect against the weeds is examined. As a result, a control effect against the weeds can be confirmed.

Example 11

Thiamethoxam is attached to soybean seeds and corn seeds. Then, a soil is packed in a pot, and the above seeds and weed seeds are sown. On the day of sowing, oxyfluorfen is uniformly applied to the soil surface. The pot is placed in a greenhouse.

On day 10 after sowing, the herbicidal effect against the weeds is examined. As a result, a control effect against the weeds can be confirmed.

Example 12

Clothianidin is attached to soybean seeds and corn seeds. Then, a soil is packed in a pot, and the above seeds and weed seeds are sown. On the day of sowing, sulfentrazone is uniformly applied to the soil surface. The pot is placed in a greenhouse.

On day 10 after sowing, the herbicidal effect against the weeds is examined. As a result, a control effect against the weeds can be confirmed.

Example 13

Thiamethoxam is attached to soybean seeds and corn seeds. Then, a soil is packed in a pot, and the above seeds and weed seeds are sown. On the day of sowing, flumioxazin is uniformly applied to the soil surface. The pot is placed in a greenhouse.

On day 10 after sowing, the herbicidal effect against the weeds is examined. As a result, a control effect against the weeds can be confirmed.

Example 14

Thiamethoxam is attached to soybean seeds and corn seeds. Then, a soil is packed in a pot, and the above seeds and weed seeds are sown. On the day of sowing, sulfentrazone is uniformly applied to the soil surface. The pot is placed in a greenhouse.

On day 10 after sowing, the herbicidal effect against the weeds is examined. As a result, a control effect against the weeds can be confirmed.

Example 15

Thiamethoxam is attached to soybean seeds and corn seeds. Then, a soil is packed in a pot, and the above seeds and weed seeds are sown. On the day of sowing, saflufenacil is uniformly applied to the soil surface. The pot is placed in a greenhouse.

On day 10 after sowing, the herbicidal effect against the weeds is examined. As a result, a control effect against the weeds can be confirmed.

Industrial Availability

Noxious organisms in the fields of soybean or corn can be controlled by the method for controlling noxious organisms according to the present invention.

The invention claimed is:

1. A method for controlling noxious organisms in a field of soybean or corn, comprising the steps of:
    treating soybean or corn seeds with clothianidin or thiamethoxam, and
    when treating soybean or corn seeds with clothianidin, treating the field with flumioxazin, sulfentrazone or saflufenacil, before or after the soybean or corn seeds treated with clothianidin are sown in the field, or
    when treating soybean or corn seeds with thiamethoxam, treating the field with flumioxazin before or after the soybean or corn seeds treated with thiamethoxam are sown in the field.

2. The method for controlling noxious organisms according to claim 1, comprising the steps of:
    treating soybean or corn seeds with clothianidin or thiamethoxam, and
    when treating soybean or corn seeds with clothianidin, treating the field with flumioxazin, sulfentrazone or saflufenacil, before the soybean or corn seeds treated with clothianidin are sown in the field, or
    when treating soybean or corn seeds with thiamethoxam, treating the field with flumioxazin before the soybean or corn seeds treated with thiamethoxam are sown in the field.

3. The method for controlling noxious organisms according to claim 1, comprising the steps of:
    treating soybean or corn seeds with clothianidin or thiamethoxam, and
    when treating soybean or corn seeds with clothianidin, treating the field with flumioxazin, sulfentrazone or saflufenacil, after the soybean or corn seeds treated with clothianidin are sown in the field, or
    when treating soybean or corn seeds with thiamethoxam, treating the field with flumioxazin after the soybean or corn seeds treated with thiamethoxam are sown in the field.

4. The method for controlling noxious organisms according to claim 1, wherein the noxious organisms are harmful arthropods.

5. The method for controlling noxious organisms according to claim 1, wherein the noxious organisms are weeds.

6. The method for controlling noxious organisms according to claim 1, wherein the soybean or corn seeds are treated with clothianidin.

7. The method for controlling noxious organisms according to claim 1 or 6, wherein the field is treated with flumioxazin.

8. A method for controlling noxious organisms in a field of soybean, comprising the steps of:
    treating soybean seeds with clothianidin or thiamethoxam, and
    when treating soybean seeds with clothianidin, treating the field with flumioxazin, sulfentrazone or saflufenacil, before or after the soybean seeds treated with clothianidin are sown in the field, or
    when treating soybean seeds with thiamethoxam, treating the field with flumioxazin before or after the soybean seeds treated with thiamethoxam are sown in the field.

9. A method for controlling noxious organisms in a field of corn, comprising the steps of:
    treating corn seeds with clothianidin or thiamethoxam, and
    when treating corn seeds with clothianidin, treating the field with flumioxazin, sulfentrazone or saflufenacil, before or after the corn seeds treated with clothianidin are sown in the field, or
    when treating corn seeds with thiamethoxam, treating the field with flumioxazin before or after the corn seeds treated with thiamethoxam are sown in the field.

* * * * *